United States Patent [19]

Grier et al.

[11] 4,119,779
[45] Oct. 10, 1978

[54] 1,3,5-s-HEXAHYDROTRISUBSTITUTED TRIAZINES

[75] Inventors: Nathaniel Grier, Englewood; Bruce E. Witzel, Westfield, both of N.J.

[73] Assignee: Merck & Co., Inc., Rahway, N.J.

[21] Appl. No.: 795,674

[22] Filed: May 11, 1977

[51] Int. Cl.$^2$ .................. C07D 263/04; C07D 405/06; C07D 405/10; C07D 263/06
[52] U.S. Cl. ................................ 544/215; 252/51.5 R
[58] Field of Search .......................................... 544/215

[56] References Cited
U.S. PATENT DOCUMENTS 2,729,680  1/1956  Anderson .............................. 260/566
3,108,101  10/1963  George et al. ........................ 544/215
3,954,750  5/1976  Coon .................................... 544/215

FOREIGN PATENT DOCUMENTS 1,067,783  5/1967  United Kingdom ..................... 544/215

Primary Examiner—John M. Ford
Attorney, Agent, or Firm—Edmunde D. Riedl; Julian S. Levitt

[57] ABSTRACT 1,3,5-s-Hexahydrotrisubstituted triazines exemplified by 1,3,5-tris(tetrahydrofurfuryl)-1,3,5-hexahydro-s-triazines are useful as antimicrobial agents particularly when employed as a component of metal-working compositions subject to fungal and bacterial attack.

15 Claims, No Drawings

1,3,5-s-HEXAHYDROTRISUBSTITUTED TRIAZINES

DISCLOSURE OF THE INVENTION

This invention relates to new and useful 1,3,5-s-hexahydrotrisubstituted triazines and to antimicrobial compositions comprising them. This invention most particularly relates to metal-working compositions protected against fungal and bacterial attack by including therein a compound of this invention.

Metal-working fluids are employed both as lubricants and heat transfer agents in operations such as cutting, drilling, rolling, broaching, drawing, extruding, and grinding. There are three basic types of these fluids: straight, soluble and synthetic.

Straight fluids comprise petroleum oils and are used as single phase systems with only slight water content. The microbial degradation problems generally occur upon storage which allows an accumulation of water as from atmospheric condensation or rain.

Soluble fluids are usually napthenic or paraffinic hydrocarbons formulated with surfactants and dispersants which produce oil-in-water emulsions on admixture with water. A variation is obtained to provide hydraulic fluids which are in reverse phase, that is, an emulsion containing water dispersed in the oil phase.

Synthetic fluids, the third type, generally comprise carboxylic and organic phosphate esters, chemically modified vegetable oils and the like replacing petroleum-based oils to provide in-use emulsions of which the external phase is water.

Additives are commonly a part of metal-working fluid formulations and include agents such as antifreeze, liquid coupling, antioxidants, corrosion inhibitors, metal deactivtors, viscosity modifiers, antifoams, extreme-pressure modifiers, oiliness, anti-wear, pour-point depressants and more. Emulsions of oil and water also require as additives, wetting-agents, surfactants, chelators for hard water metal ions and stabilizers such as thickening agents.

Most of the constituents of metal-working fluids outlined when admixed with water serve as nutrients to support microbial growth.

Unless controlled, these organisms affect the performance of a fluid as, for example, by lowering the pH or breaking the emulsion. A low pH fluid is corrosive to metal and the resultant metal ions form precipitates with surfactants which tend to break down the emulsion. Whether or not the performance of the metal-working fluid is spoiled by bacterial or fungal action, it often becomes so foul smelling that it must be discarded. Such disposal, possibly involving thousands of gallons of a malodorous oily emulsion presents a considerable ecological problem and economic loss. Furthermore, there is an increasing trend toward the use of solubilized oils which are more susceptible to attack by microorganisms as compared to the straight mineral oils. Regulations on effluent discharges increase the need for metal-working fluids protected with efficient biocides, because untreated fluids go rancid more rapidly, requiring more frequent disposal and thus contributing to pollution.

A great variety of microorganisms are found in metal-working fluids, but the anaerobic sulfate reducers and fungi are particularly troublesome to control. Others include the aerobic gram-negative bacteria, e.g., coliforms, and particularly *Pseudomonas*. Actual spoilage of the fluids appears to be associated with *Pseudomonas* and sulfate reducing bacteria such as *Desulfovibrio desulfuricans*.

Heretofore, biocides used to protect metal-working fluids have included tris(hydroxymethyl)nitromethane; organic iodine; hexamethylenetetramine derivatives; o-phenylphenol; sodium o-phenylphenate; sodium 2,4,5-trichlorophenate; 2,3,4,6-tetrachlorophenol; dimethoxane; 1,2-benzisothiazolin-3-one; hexahydro-1,3,5-tris-(2-hydroxyethyl)-s-triazine; and zinc pyridinethione. However, most have proven unsatisfactory because of narrow spectrum, potential toxicities, high cost or other important considerations. In practice, biocides are often added at least twice, first by the formulators of the fluids themselves for preservation and then by the user to additionally extend service life.

Under typical operating conditions, there are problems of contamination from organic matter, dirt, metal cuttings, and other debris. An ideal product would function properly despite this and present no environmental disposal problems. Therefore, the object of this invention is to provide a biocide for metal-working fluids which is economical and stable in use; effective over a wide pH range; resists water hardness; does not induce foam; inhibits a broad spectrum of microorganisms, especially gram-negative bacteria and fungi; and is non-irritating to skin and has a low acceptable toxicity level to users and upon discharge as effluent.

The biocidal compounds of this invention have the structure:

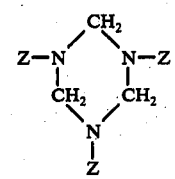

where Z is $R_3$ or

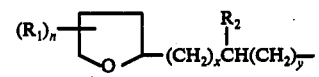

where $R_1$ is hydrogen, $C_1$–$C_8$ alkyl, $C_1$–$C_8$ hydroxyalkyl, $C_1$–$C_8$ alkoxyloweralkyl, phenyl loweralkyl, phenyl and phenyl where the phenyl is monosubstituted with halogen, nitro, loweralkyl, and loweralkoxy and where $n$ is an integer of from 1 to 3;

$R_2$ is hydrogen, $C_1$–$C_8$ alkyl, phenyl loweralkyl, and phenyl, $x$ and $y$ are each integers from 0 to 4 and the sum of $x$ and $y$ is 0 to 4;

$R_3$ is hydrogen, hydroxyloweralkyl, and $C_1$ to $C_8$ alkyl, provided no more than one Z is $R_3$.

Most suitably $R_1$ is hydrogen, loweralkyl, hydroxyloweralkyl, loweralkoxyloweralkyl, phenyl loweralkyl, phenyl, and phenyl where the phenyl is mono-substituted with halogen, nitro, loweralkyl, loweralkoxy and $n$ is 1.

As used herein the term "halogen" includes fluoro, chloro, bromo and iodo; and the prefix "lower" includes groups of from 1 to 4 carbon atoms such as methyl, ethyl, propyl, isopropyl, butyl, isobutyl and t-butyl, $C_1$–$C_8$ includes the foregoing groups such as methyl, ethyl, etc. as well as amyl, hexyl, 2-ethylehxyl, heptyl, octyl and the like.

R₂ most suitably is hydrogen, loweralkyl, phenyllow-eralkyl, phenyl, or benzyl, and all Z's are other than R₃, while in the most preferred embodiments, $n$ is 1, $x$ is 0, $y$ is 0, and R₂ is hydrogen.

The compounds of formula I are prepared by the reaction of a primary amine of formula II:

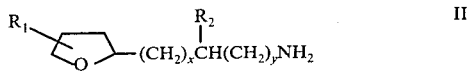

II with formaldehyde or a formaldehyde releasing agent. Usually, a 20%–30% molar excess of formaldehyde or an equivalent excess of a formaldehyde releasing agent is used as compared to the amine in a temperature range of from 10° C.–80° C. and reaction times ranging from a half-hour to ten hours. The reaction may be run in the presence of water and/or inert hydrocarbon solvents such as benzene or toluene, with or without 5–20 mole percent of inorganic base such as sodium or potassim hydroxide as compared to primary amines. Generally, the amine and aqueous base are first admixed, cooled to 10° C.–20° C. and the formaldehyde added in small increments while maintaining the reaction mixture at or below about 20° C.–25° C. The product, if water soluble, can be isolated by saturating the mixture with sodium chloride and then extracting several times with benzene. The organic layer is separated, washed with a small volume of water, dried over anhydrous magnesium sulphate, filtered and the solvent removal by distillation. Further, purification of product, if desired, can be obtained by fractional distillation under reduced pressure or if solid by recrystallization.

Another variation of procedure utilizes the addition of a solution of amine in water (20%–70% by wt. amine) or water-dioxane over a period of 2–3 hours to a solution of formaldehyde in water (20%–37% by wt. formaldehyde) in a molar ratio of approximately 1 while maintaining the reaction temperature at 35° C.–45° C. The mixture, after complete addition was stirred an additional hour at 25° C.–30° C. and the organic phase then caused to separate upon the addition of sufficient flake potassium hydroxide to produce a 20% by weight solution in the aqueous phase. The separated oil phase was then isolated and distilled under reduced pressure to obtain a relatively pure s-hexahydrotriazine derivative.

In yet another general procedure 1 mole of primary amine is cooled in an ice bath, treated with 1 mole of an aqueous 37% by weight formaldehyde solution by gradual addition to dissipate the evolved heat of reaction. Then, an equal volume of benzene is added and azeotropic distillation is utilized for continuous water removal, and return of the benzene. After all of the water has been removed the mixture is filtered and the solvent stripped off. Any amine reactant and by-products are eliminated by heating at 0.5 to 1 mm. pressure to temperature below the boiling point or decomposition temperature of the product. If paraformaldehyde is used instead of aqueus formaldehyde the water of condensation is removed by azeotropic distillation with benzene as outlined.

GENERAL PROCEDURE

Preparation of 1,3,5-Trisubstituted-1,3,5-hexahydro-s-triazines

A. To a 12 l. three-necked flask equipped with a stirrer, thermometer, and a dropping funnel, two liters of water and 300 g. of sodium hydroxide were added. After the sodium hydroxide had dissolved, two liters of benzene was introduced. With external cooling, 40 moles of a tetrahydrofuran substituted primary amine was added and the mixture cooled to 20° C.–25° C. Formalin (35%–40%) (3600 g.) was added slowly while maintaining the temperature below 25° C. When the formalin addition was finished and the reaction completed, salt and additional benzene were added when necessary to ensure two distinct layers. The benzene layer was separated, dried over magnesium sulfate and the benzene removed under vacuum. The products could be purified by fractional distillation under reduced pressure.

B. 1 Mole of primary amine (tetrahydrofuran substituted) is cooled in an ice-bath and reacted with 1.02 moles of a 37% aqueous formaldehyde solution. The heat of reaction is released shortly upon admixing. Then, 300 ml. of benzene is added, the mixture heated under reflux and the water continuously removed by azeotropic distillation using a Dean-Stark trap. The mixture is filtered, the solvent removed by distillation and the residue stripped of volatiles at a pressure of 0.5–2 mm. to an internal temperature of 10° C. below the product boiling point or decomposition temperature.

C. 1 Mole of paraformaldehyde was added slowly with agitation to 1 mole of a tetrahydrofuran substituted primary amine. The water of condensation was removed by distillation under reduced pressure. The residue can be dissolved in an inert solvent such as naphtha or benzene, filtered free of insolubles and then stripped of solvent. Further purification can be obtained by fractional distillation under reduced pressure or recrystallization.

D. For 1,3,5-substituted-1,3,5-hexahydro-s-triazines which have different substituents at the 1, 3 or 5 position the above procedures may be employed. The two primary amines are then used as mixtures in the molar ratio to provide the desired proportion of the two side chains in the end product. The combined molar ratio will still be equal in sum to that of the formaldehyde employed. For example, 0.67 mole of a tetrahydrofuran substituted primary amine mixed with 0.33 mole of a second primary amine and reacted with 1 mole of formaldehyde will provide a 1,3,5-hexahydro-s-triazine with two of the ring nitrogens substituted with a tetrahydrofuran containing group and the third nitrogen bearing the moiety corresponding to the other primary amine substituent.

Preparation of 1,3,5-Tris(tetrahydrofurfuryl)-1,3,5-hexahydro-s-triazine 30.3 G. (0.3 mole) Tetrahydrofurfurylamine was dissolved in 250 ml. of ethyl alcohol. There was then added over a 7 minute period using good agitation 25 g. (0.3 mole) of 37% aqueous formaldehyde. The exothermic reaction caused a temperature rise of from 25° C.–38° C. After complete addition the reaction mixture was heated to an internal temperature of 57° C. and maintained at 57° C. for 1½ hours. It was cooled to 25° C., and after standing overnight the mixture was stripped of volatiles by finally heating in a bath at 47° C. and under 1–5 mm. pressure. The residual oil, 34.9 g., was of analytical purity, and thin layer chromatography on silica gel with development using a mixture of 5% methyl alcohol and 95% chloroform each by volume confirmed the result, evidencing a single spot upon iodine staining, $R_f=0.54$.

The above procedure is utilized with an equal molar ratio of primary amine to formaldehyde for the synthesis of the following:

| Reactant | Product |
| --- | --- |
| R'-amine | 1,3,5-tris-R'-hexahydro-1,3,5-s-triazine | where R' is:
2-Methyltetrahydrofurfuryl
4-Isopropyltetrahydrofurfuryl
5,5-Dimethyltetrahydrofurfuryl
4-Methyl-5-ethyltetrahydrofurfuryl
5-Hydroxymethyltetrahydrofurfuryl
5-Benzyltetrahydrofurfuryl
5-(4-Methoxyphenyl)tetrahydrofurfuryl
5-Hydroxymethyl-3-methyltetrahydrofurfuryl
5-Methoxymethyltetrahydrofurfuryl
5-n-Octyloxymethyltetrahydrofurfuryl
α-Methyltetrahydrofurfuryl
α-Benzyltetrahydrofurfuryl
α-(1-Naphthylmethyl)tetrahydrofurfuryl
α-(4-Nitrophenyl)tetrahydrofurfuryl
α-Phenyltetrahydrofurfuryl
α-(4-Chlorophenyl)tetrahydrofurfuryl
3-(2-Tetrahydrofuryl)propyl
3-(2-Tetrahydrofuryl)heptyl
3-Benzyl-4-(2-tetrahydrofuryl)butyl
3-Benzyl-4-(2-tetrahydrofuryl)pentyl
1-Phenyl-2-(2-tetrahydrofuryl)ethyl
1-Phenyl-2-(2-tetrahydrofuryl)pentyl s-Hexahydrotriazine according to Formula I in which only two of the Z moieties contain a tetrahydrofuryl moiety can be prepared using the methods described with the modification that the primary amine reactant comprises a mixture of primary amines in a molar ratio corresponding to that of the desired end product. For example, if one Z is to be 2-hydroxyethyl then the primary amine reactant, 1 mole total, would be a mixture of 0.33 mole ethanolamine and 0.67 mole of a tetrahydrofurylsubstituted amine. This would then be reacted with 1 mole of formaldehyde.

Additional products made in this manner include:
1-(2-Hydroxyethyl)-3,5-di-(tetrahydrofurfuryl)hexahydro-1,3,5-s-triazine
1-Methyl-3,5-di-(tetrahydrofurfuryl)hexahydro-1,3,5-s-triazine
1,3-di-(α-Benzyltetrahydrofurfuryl)-5-(2-hydroxyethyl)-hexahydro-1,3,5-s-triazine
1-Ethyl-3,5-di-(5-methoxymethyltetrahydrofurfuryl)-hexahydro-1,3,5-s-triazine
1-(3-Hydroxypropyl)-3,5-di-[3-(2-tetrahydrofuryl)-propyl]hexahydro-1,3,5-s-triazine The compositions of metal-working fluids can vary broadly depending upon applications. General utility emulsifiable oils usually contain 80%–90% by weight of a petroleum hydrocarbon oil, 5%–18% of an emulsifying agent soluble in the oil which may be oleic acid, a sulphated mineral oil, a polyethoxylated substituted phenol and others, together with a small percentage, usually less than 2%, of water to prevent gelling. When freezing point depressants are formulated into the oil base, and such agents include methyl alcohol, ethylene glycol, propylene glycol, dipropyleneglycol or hexyleneglycol, a sufficient quantity is used so that upon emulsification of the oil in from 10–50 parts of water per 1 part of oil there is present from 1 to 100 parts of freezing point depressant per 100 parts of water comprising the aqueous phase of the emulsion.

Extreme pressure additives commonly employed include graphite, molybdenum sulfide, sulfuretted oils, fatty amine salts of long chain phosphate acid esters, talc and others. Antioxidants are based primarily upon aromatic compounds containing an air-sensitive group such as hydroxy, amino or alkoxy along with oil-solubilizing alkyl ring substituents. 2,6-Di-tert. butylphenol, N-butyl para-aminophenol, p-nonylphenol and 1,5-dihydroxynaphthalene are a few examples.

Corrosion inhibitors presently in popular use are presented problems of potential toxicity. Apparently, morpholine and other secondary or tertiary amines interact with inorganic nitrites also added as corrosion inhibitors to produce carcinogenic nitrosamines. Other corrosion inhibitors such as inorganic salts of 2-mercaptobenzothiazole, of alkenylsuccinic acids and of stearic acid, butyl esters of lipid-soluble carboxylic acids and various polysiloxanes will probably be preferably added.

Some representative compositions are:

| Cutting Fluid | Parts by Wt. |
| --- | --- |
| Triethanolamine | 20 |
| Caprylic Acid | 3 |
| Poly(oxyethylene)glycol | 7 |
| Sodium 2-Mercaptobenzothiazole | 3 |
| 1,3,5-Tris(tetrahydrofurfuryl)-1,3,5-hexahydro-s-triazine | 0.5 |
| Water | 66.5 |

For use the fluid is diluted 1 to 5 with water.

| | Parts by Wt. |
| --- | --- |
| Mineral Oil ($d_{20}$, 0.915) | 80 |
| Petroleum Sulfonate (mol. wt. 400) as 70% Aq. Solution | 14 |
| Ethoxylated (5 Moles Ethylene Oxide) Oleyl Alcohol | 3.5 |
| 1,3,5-Tris(4-isopropyltetrahydrofurfuryl)-1,3,5-hexahydro-s-triazine | 2 |
| 2,6-Ditertiarybutyl-p-cresol | 0.5 |

For use 1 part of the fluid is diluted with 20–40 parts of water.

| Grinding Fluid | Parts by Wt. |
| --- | --- |
| Poly(ethoxylated) Castor Oil | 50 |
| Dipropylene Glycol | 50 |
| Water | 150 |
| 1,3,5-Tris-(5-methoxymethyltetrahydrofurfuryl)-1,3,5-hexahydro-s-triazine | 0.15–0.6 |

| | Parts by Wt. |
| --- | --- |
| Poly(ethoxylated) Castor Oil | 25 |
| Hexylene Glycol | 20 |
| Dipropylene Glycol | 45 |
| Petroleum Sulfonate | 5 |
| Poly(oxyethylene)octadecylamine | 2 |
| 1,3,5-Tris-(tetrahydrofurfuryl)-1,3,5-hexahydro-s-triazine | 0.3–1. |
| Dibenzyl Disulfide | 2 |
| Water | 600 |
| Mold Release Formulation | Parts by Wt. |
| Dow-Corning Co. Silicone Oil 200 (1000 centistoke) | 200 |
| Poly(Acrylic Acid) | 2 |
| Dodecylamine | 1 |
| Sodium Hydroxide (10% Solution) | 6 |
| 1,3,5-Tris[3-(2-tetrahydrofuryl)-propyl]-1,3,5-hexahydro-s-triazine | 0.1–0.4 |
| Water | 200 |

Hydraulic Fluid — Lubricant

Oil-in-water emulsions are prepared from 80 parts water, 20–99 parts mineral oil and 0.2–10 parts ester obtained by a $C_{50+}$ alkylsubstituted succinic acid esterification with, for example, sorbitan monooleate or other polyols.

|  | Parts by Wt. |
| --- | --- |
| Lubricating Oil SAE 30 | 286 |
| Soybean Lecithin | 1.8 |
| Zinc Diisooctylphosphorodithioate | 3 |
| Primary tert. $C_{11}$-$C_{14}$ Alkylamine | 0.6 |
| Sorbitan Oleate, Polyisobutenyl-succinate | 9 |
| Silicone Antifoam | .0075 |
| 1,3,5-Tris(tetrahydrofurfuryl)-1,3,5-hexahydro-s-triazine | 0.3-30 | for dilutions in water ranging from 1:1 to 1:100.

In use the compounds of this invention are added to a metal-working oil composition or to the emulsions obtained therefrom upon admixing with water so that a concentration of from 50 to 5000 parts per million of antimicrobial is obtained at final use dilutions. Generally, cutting oil concentrates are diluted with 10 to 50 parts by weight of water for end use application as for machining operations. At the lower dilution ratio, in round numbers, 10,000 ppm of the compounds of this invention would be contained in the oil concentrate so that upon addition of 1 part of oil to 9 parts of water a final concentration of 1,000 ppm would result. The antimicrobial can be added also after dilution.

For mold release agents or hydraulic fluids, it is preferable to incorporate the antimicrobial during product formulation. These preparations usually contain sufficient water to promote microbial growths prior to usage and require protection against biodegradation in the package or on storage. The ingredients employed may carry microbial inocula or simply air-born organisms may initiate growths.

Under laboratory assay conditions in nutrient test media the compounds of this invention are inhibitory to gram-positive, gram-negative bacteria, yeast and fungi at conventrations of 50–500 ppm. Five typical cutting fluids which includes three oil-in-water emulsions, one preformed emulsion and one straight chemical solution, all at dilutions from the concentrate of 1 to 20, were used to demonstrate the utility of our compounds. At concentrations of 0.05 and 0.1% by weight of 1,3,5-tris-(tetrahydrofurfuryl)-1,3,5-hexahydro-s-triazine in each diluted formulation, and initial bacterial population obtained with spoiled oil inocula to provide $10^8$–$10^9$ organism per ml., complete kill was obtained. In the same systems having mixed fungal populations of $10^3$–$10^5$ per ml., sterility was achieved with 0.1% biocide concentration and very marked reductions with 0.05% biocide. In other experiments with metal-working fluids, a single dosage of 0.1% of biocide provided sterility for several months despite a weekly challenge with pure microbial cultures and spoiled oil inocula. In the same test system, a commercial product, 1,3,5-tris-(2-hydroxyethyl)-1,3,5-hexahydro-s-triazine at the same and higher concentrations failed to suppress fungal growth initially and throughout the test period. Similarly, 1,3,5-tri-(ethyl)-1,3,5-hexahydro-s-triazine also failed.

Other aqueous systems which are vulnerable to microbial degradation and which may be protected against biodeterioration with the hexahydro-s-triazines of this invention include aqueous adhesives, pigment dispersions, paints, cooling tower systems, drilling muds, enhanced oil recovery brines and pusher fluids, papermill waters and as antimicrobials for pathogenic microorganisms on seeds and plants.

What is claimed is:

1. A compound having the formula:

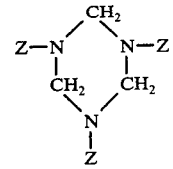

where each Z is $R_3$ or

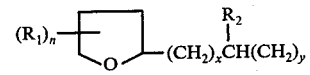

where $R_1$ is hydrogen, $C_1$–$C_8$ alkyl, $C_1$–$C_8$ hydroxyalkyl, $C_1$–$C_8$ alkoxyloweralkyl, phenyl loweralkyl, phenyl and phenyl where the phenyl is monosubstituted with halogen, nitro, loweralkyl and loweralkoxy; where $n$ is an integer of from 1 to 3;

$R_2$ is hydrogen, $C_1$–$C_8$ alkyl, phenyl loweralkyl, and phenyl, $x$ and $y$ are each integers from 0 to 4 and the sum of $x$ and $y$ is 0 to 4; and $R_3$ is hydrogen, hydroxyloweralkyl, and $C_1$–$C_8$ alkyl, provided no more than one Z is $R_3$.

2. A compound according to claim 1 where each Z is

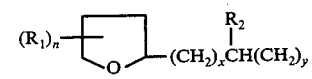

where $R_1$ is hydrogen, $C_1$–$C_8$ alkyl, $C_1$–$C_8$ hydroxyalkyl, $C_1$–$C_8$ alkoxyloweralkyl, phenyl loweralkyl, phenyl and phenyl substituted with halogen, nitro, loweralkyl and loweralkowy where $n$ is an integer of from 1 to 3;

$R_2$ is hydrogen, $C_1$–$C_8$ alkyl, phenyl loweralkyl, and phenyl, $x$ and $Y$ are each integers from 0 to 4 and the sum of $x$ and $y$ is 0 to 4.

3. A compound according to claim 2 where $R_1$ is hydrogen, loweralkyl, hydroxyalkyl, loweralkoxyloweralkyl, phenylloweralkyl or phenyl or phenyl or benzyl monosubstituted with halogen, nitro, loweralkyl or loweralkoxy.

4. A compound according to claim 2 where $n$ is 1.

5. A compound according to claim 2 where the sum of $x$ and $y$ is 1.

6. A compound according to claim 2 where $R_2$ is hydrogen.

7. A compound according to claim 2 where $R_2$ is hydrogen and the sum of $x$ and $y$ is 0.

8. A compound according to claim 1 where one Z is $R_3$ and $R_3$ is hydroxyloweralkyl.

9. A compound according to claim 1 where one Z is $R_3$ and $R_3$ is loweralkyl.

10. A compound according to claim 1 where one Z is $R_3$ and $R_3$ is hydrogen.

11. 1,3,5-Tris-(tetrahydrofurfuryl)-1,3,5-hexahydro-s-triazine.

12. 1,3,5-Tris-(5-hydroxymethyltetrahydrofurfuryl)-1,3,5-hexahydro-s-triazine.

13. 1,3,5-Tris-($\alpha$-methyltetrahydrofurfuryl)-1,3,5-hexahydro-s-triazine.

14. 1-(2-Hydroxyethyl)-3,5-di-(tetrahydrofurfuryl)-hexahydro-1,3,5-s-triazine.

15. 1-Ethyl-3,5-di-5-(methoxymethyltetrahydrofurfuryl)hexahydro-1,3,5-s-triazine.

* * * * *